United States Patent [19]

Velenyi et al.

[11] Patent Number: 4,727,205

[45] Date of Patent: Feb. 23, 1988

[54] PROCESS FOR CONVERTING METHANE AND/OR NATURAL GAS TO MORE READILY TRANSPORTABLE MATERIALS

[75] Inventors: Louis J. Velenyi, Lyndhurst; Christos Paparizos, Willowick, both of Ohio

[73] Assignee: The Standard Oil Company, Cleveland, Ohio

[21] Appl. No.: 901,651

[22] Filed: Aug. 28, 1986

[51] Int. Cl.$^4$ .............................................. C07C 2/00
[52] U.S. Cl. .................................. 585/407; 585/500; 585/700; 585/943
[58] Field of Search ............... 585/500, 943, 414, 520, 585/700, 407

[56] References Cited

U.S. PATENT DOCUMENTS

| | | | |
|---|---|---|---|
| 2,180,672 | 11/1939 | Frey | 585/943 |
| 2,656,307 | 10/1953 | Findlay | 585/943 |
| 3,452,114 | 6/1969 | Friz et al. | 585/943 |
| 3,720,600 | 3/1973 | Mansfield et al. | 208/47 |
| 4,116,812 | 9/1978 | Godar et al. | 208/48 |
| 4,497,970 | 2/1985 | Young | 585/417 |
| 4,513,164 | 4/1985 | Olah | 585/415 |
| 4,542,253 | 9/1985 | Kaplan et al. | 585/650 |
| 4,544,785 | 10/1985 | Withers et al. | 585/500 |
| 4,592,826 | 6/1986 | Ganguli | 208/407 |

*Primary Examiner*—William R. Dixon, Jr.
*Assistant Examiner*—Cynthia A. Prezlock
*Attorney, Agent, or Firm*—Larry W. Evans; David J. Untener; Raymond F. Keller

[57] ABSTRACT

The invention relates to a process for converting light hydrocarbon feedstocks such as methane and/or natural gas, to higher molecular weight hydrocarbon products that are more readily handleable and transportable. The process comprises heating a gaseous mixture comprising said light hydrocarbon feedstocks and a minor, effective amount of at least one ether or thioether compound at a temperature of at least about 800° C. for a period of time effective to provide said higher molecular weight liquid hydrocarbon product. The invention also relates to the higher molecular weight liquid products obtained by the process of the invention.

34 Claims, No Drawings

PROCESS FOR CONVERTING METHANE AND/OR NATURAL GAS TO MORE READILY TRANSPORTABLE MATERIALS

TECHNICAL FIELD

This invention relates to a thermal process for converting methane and/or natural gas to liquid higher molecular weight products. This invention further relates to the use of ethers and thioethers to assist such conversions where the yield of liquid products is enhanced.

BACKGROUND OF THE INVENTION

A major source of methane is natural gas which typically contains about 40-95% methane depending on the particular source. Other constituents include about 10% of ethane with the balance being made up of $CO_2$ and smaller amounts of propane, the butanes, the pentanes, nitrogen, etc.

Primary sources for natural gas are the porous reservoirs generally associated with crude oil reserves. From these sources come most of the natural gas used for heating purposes. Quantities of natural gas are also known to be present in coal deposits and are by-products of crude oil refinery processes and bacterial decomposition of organic matter. Natural gas obtained from these sources is generally utilized as a fuel at the site.

Prior to commercial use, natural gas must be processed to remove water vapor, condensible hydrocarbons and inert or poisonous constituents. Condensible hydrocarbons are generally removed by cooling natural gas to a low temperature and then washing the natural gas with a cold hydrocarbon liquid to absorb the condensible hydrocarbons. The condensible hydrocarbons are typically ethane and heavier hydrocarbons. This gas processing can occur at the wellhead or at a central processing station. Processed natural gas typically comprises a major amount of methane, and minor amounts of ethane, propane, the butanes, the pentanes, carbon dioxide and nitrogen. Generally, processed natural gas comprises from about 70% to more than about 95% by volume of methane. Natural gas is used principally as a source of heat in residential, commercial and industrial service.

Most processed natural gas is distributed through extensive pipeline distribution networks. As natural gas reserves in close proximity to gas usage decrease, new sources that are more distant require additional transportation. Many of these distant sources are not, however, amendable to transport by pipeline. For example, sources that are located in areas requiring economically unfeasible pipeline networks or in areas requiring transport across large bodies of water are not amendable to transport by pipeline. This problem has been addressed in several ways. One such solution has been to build a production facility at the site of the natural gas deposit to manufacture one specific product. This approach is limited as the natural gas can be used only for one product, preempting other feasible uses. Another approach has been to liquefy the natural gas and transport the liquid natural gas in specially designed tanker ships. Natural gas can be reduced to 1/600th of the volume occupied in the gaseous state by such cryogenic processing, and with proper procedures, safely stored or transported. These processes, which involve liquefying natural gas to a temperature of about $-162°$ C., transporting the gas, and revaporizing it are complex and energy intensive.

Still another approach has been the conversion of natural gas to higher molecular weight hydrocarbons that can be easily handled and transported, preferably substantially liquid hydrocarbons. The conversion of natural gas to higher order hydrocarbons, especially ethane and ethylene, would retain the material's versatility for use as precursor materials in chemical processing. Known dehydrogenation and polymerization processes are available for the further conversion of ethane and ethylene to liquid hydrocarbons. In these ways, easily transportable commodities may be derived directly from natural gas at the wellhead. A drawback in implementing such processes has been in obtaining a sufficient conversion rate of natural gas to higher molecular weight hydrocarbons.

The conversion of methane to higher molecular weight hydrocarbons at high temperatures, in excess of about 1200° C. is known. These processes are, however, energy intensive and have not been developed to the point where high yields are obtained even with the use of catalysts. Some catalysts that are useful in these processes (e.g., chlorine) are corrosive under such operating conditions.

Low temperature reactions (e.g., to 250° C. and 500° C.) of hydrocarbon feedstocks to higher molecular weight hydrocarbons are described in U.S. Pat. Nos. 4,433,192; 4,497,970; and 4,513,164. The processes described in these patents utilize heterogeneous systems and solid acid catalysts. In addition to the solid acid catalysts, the reaction mixtures described in the '970 and '164 patents include oxidizing agents. Among the oxidizing agents disclosed are air, $O_2$-$O_3$ mixtures, S, Se, $SO_3$, $N_2O$, NO, $NO_3$, F, etc.

The catalytic oxidative coupling of methane at atmospheric pressure and temperatures of from about 500° C. to 1000° C. has been investigated by G. E. Keller and M. M. Bhasin. These researchers reported the synthesis of ethylene via oxidative coupling of methane over a wide variety of metal oxides supported on an alpha alumina structure in *Journal of Catalysis*, 73, 9-19 (1982). This article discloses the use of single component oxide catalysts that exhibited methane conversion to higher order hydrocarbons at rates no greater than 4%. The process by which Keller and Bhasin oxidized methane was cyclic, varying the feed composition between methane and nitrogen and air (oxygen) to obtain higher selectivities.

The conversion of methane to higher molecular weight hydrocarbons using metal oxide catalysts and oxides of carbon which are generated from the hydrocarbon is described in U.S. Pat. No. 2,180,672. The conversion generally is carried out at temperatures of from about 150°-350° C., and the oxides of carbon are consumed in the reaction.

U.S. Pat. No. 1,677,363 describes the conversion of methane or natural gas to ethylenic hydrocarbons by heating a thin stream of methane or natural gas to a temperature not exceeding 950° C. U.S. Pat. No. 4,304,657 describes a process for converting feedstocks comprising aliphatic fractions boiling 70° C. Typically, the feedstock may be napthas, coker gasolines, FCC gasoline and pyrolysis gasolines. The process uses aromatization catalysts and a diluent which may be $CO_2$, CO or nitrogen, and the dilution is in a molar ratio of diluent to feed of from about 20:1 to 1:1. Preferred dilutions are 10:1 to 5:1 of diluent to fuel.

Methods for converting methane to higher molecular weight hydrocarbons at temperatures in the range of about 500° C. to about 1000° C. are disclosed in U.S. Pat. Nos. 4,443,644; 4,443,645; 4,443,646; 4,443,647; 4,443,648; and 4,443,649. The processes taught by these references provide relatively high selectivities to higher order hydrocarbons but at relatively low conversion rates, on the order of less than about 4% overall conversion. In addition to synthesizing hydrocarbons, the processes disclosed in these references also produce a reduced metal oxide which must be frequently regenerated by contact with oxygen. The preferred processes taught by these references entail physically separate zones for a methane contacting step and for an oxygen contacting step, with the reaction promoter recirculating between the two zones.

U.S. Pat. Nos. 4,172,810; 4,205,194; and 4,239,658 disclose the production of hydrocarbons including ethylene, benzene, ethane, propane and the like, in the presence of a catalyst-reagent composition which comprises: (1) a group VIII noble metal having an atomic number of 45 or greater, nickel, or a group Ib noble metal having an atomic number of 47 or greater; (2) a group VIb metal oxide which is capable of being reduced to a lower oxide; and (3) a group IIa metal selected from the group consisting of magnesium and strontium composited with a passivated, spinel-coated refractory support or calcium composited with a passivated, non-zinc containing spinel-coated refractory support. The feed streams used in the processes disclosed in these patents do not contain oxygen. Oxygen is avoided for the purposes of avoiding the formation of coke in the catalyst. Oxygen is generated for the reaction from the catalyst; thus periodic regenerations of the catalysts are required.

U.S. Pat. No. 4,450,310 discloses a methane conversion process for the production of olefins and hydrogen comprising contacting methane in the absence of oxygen and in the absence of water at a reaction temperature of at least 500° C. with a catalyst comprising the mixed oxides of a first metal selected from lithium, sodium, potassium, rubidium, cesium and mixtures thereof, a second metal selected from beryllium, magnesium, calcium, strontium, barium, and mixtures thereof, and optionally a promoter metal selected from copper, rhenium, tungsten, zirconium, rhodium, and mixtures thereof.

It would be advantageous to provide a process for converting light hydrocarbons such as methane and/or natural gas to higher molecular weight liquid hydrocarbons that are more readily handleable and transportable.

SUMMARY OF THE INVENTION

A process is described for converting methane and/or natural gas to higher molecular weight liquid hydrocarbon products that are more readily handleable and transportable. The process comprises heating a gaseous mixture comprising said methane and/or natural gas and a minor effective amount of at least one ether or thioether compound at a temperature of at least about 800° C. for a period of time effective to provide said higher molecular weight hydrocarbon product. The invention also relates to the higher molecular weight liquid products obtained by the process of the invention.

DESCRIPTION OF THE PREFERRED EMBODIMENTS

The light hydrocarbon feedstocks that are converted to liquid hydrocarbons in accordance with the process of the invention are typically methane and/or natural gas. The methane which is treated in accordance with this invention may contain other materials such as ethane, ethylene, propane, etc. The natural gas that can be used can be either wellhead natural gas, as discussed above, or processed natural gas. The composition of processed natural gas varies with the needs of the ultimate user. A typical processed natural gas composition contains about 75–80% by volume methane, up to about 15% by volume of $CO_2$, about 5 to 10% by volume of ethane, the balance being made up of propane, butane and nitrogen.

The conversion of the light hydrocarbon feedstocks to liquid hydrocarbon products is conducted in the presence of an effective amount of at least one ether or thioether. The ether or thioether assists in the conversion of the methane and/or natural gas to higher molecular weight liquid hydrocarbons. The presence of the ether or thioether results in higher conversion to liquid products, and the amount of carbon formed in the pyrolysis reaction in relation to the amount of methane converted is reduced.

The ether and thioethers which are useful in assisting in the conversion of a methane and/or natural gas to higher molecular weight liquid hydrocarbons may be any of the organic ethers and thioethers represented by the general formula

$$R^1XR^2$$

wherein X is oxygen or sulfur and $R^1$ and $R^2$ are each independently hydrocarbyl groups. Where $R^1$ and/or $R^2$ are hydrocarbyl groups containing oxygen atoms, the ethers and thioethers useful in the present invention are polyethers. Preferably, X is oxygen and $R^1$ and $R^2$ are hydrocarbyl groups containing up to about 10 carbons atoms.

As used above, and elsewhere in the specification and claims, the terms "hydrocarbon group" or "hydrocarbyl group" denote a group having a carbon atom directly attached to the remainder of the molecule and having predominantly hydrocarbon character within the context of this invention. Such groups include the following:

(1) Hydrocarbon groups; that is, aliphatic, (e.g., alkyl or alkenyl), alicyclic (e.g., cycloalkyl or cycloalkenyl), aromatic, aliphatic- and alicyclic-substituted aromatic, aromatic-substituted aliphatic and alicyclic groups, and the like, as well as cyclic groups wherein the ring is completed through another portion of the molecule (that is, any two indicated substituents may together form an alicyclic group).

(2) Substituted hydrocarbon groups; that is, groups containing non-hydrocarbon substituents which, in the context of this invention, do not alter the predominantly hydrocarbon character of the group. Those skilled in the art will be aware of suitable substituents; examples include nitro, hydroxy, RO—, RS—, ROC(O)— and RC(O)—, (R being a hydrocarbon group and especially a lower alkyl group.

(3) Hetero groups; that is, groups which, while predominantly hydrocarbon in character within the context of this invention, contain atoms other than carbon in a chain or ring otherwise composed of carbon atoms. Suitable hetero atoms will be apparent to those skilled in the art and include, for example, nitrogen, oxygen and sulfur.

In general, no more than about three substituents or hetero atoms, and preferably no more than one, will be present for each 10 carbon atoms in the hydrocarbyl group.

The hydrocarbyl groups of the ethers and thioethers useful in the present invention may be aliphatic, cycloaliphatic or aromatic hydrocarbyl groups, and aliphatic groups are preferred. The aliphatic groups may be saturated or unsaturated groups and thus, the aliphatic groups may be alkyl groups, alkenyl groups or alkynyl groups.

The aliphatic groups $R^1$ and $R^2$ are exemplified by methyl, ethyl, n-propyl, isopropyl, n-butyl, isobutyl, amyl, hexyl, octyl, nonyl, decyl, benzylmethoxymethyl, ethoxymethyl, ethoxyethyl, etc. Examples of alkenyl groups include allyl, vinyl, ethynyl, propenyl, etc. Examples of aromatic groups include phenyl, 4-aminophenyl, 4-bromophenyl, naphthyl, etc. In one preferred embodiment, $R^1$ and $R^2$ are independently alkyl groups containing up to about 6 carbon atoms.

Specific examples of ethers useful in the process of the present invention include dimethyl ether, diethyl ether, di-n-propyl ether, di-n-butyl ether, di-hexyl ether, diheptyl ether, methyl ethyl ether, methyl n-propyl ether, methyl n-butyl ether, ethyl butyl ether, allyl methyl ether, allyl ethyl ether, allyl propyl ether, allyl octyl ether, divinyl ether, butyl vinyl ether, ethyl 1-propenyl ether, ethoxyacetylene, dibenzyl ether, etc. Examples of aliphatic and alicyclic thioethers include dimethyl sulfide, diethyl sulfide, methyl butyl sulfide, methyl sec-butyl sulfide, methyl t-butyl sulfide, methyl isobutyl sulfide, methyl isopropyl sulfide, methyl propyl sulfide, ethyl methyl sulfide, ethyl vinyl sulfide, 2-chloro-ethyl n-butyl sulfide, 2-chloroethyl methyl sulfide, chloromethyl methyl sulfide, 2-hydroxyethyl methyl sulfide, 2-hydroxyethyl propyl sulfide, 2-hydroxyhexyl n-butyl sulfide, dicyclohexyl sulfide, etc.

Aryl and mixed alkyl aryl ethers are exemplified by methyl phenyl ether, diphenyl ether, etc.

As mentioned above, the hydrocarbyl groups $R^1$ and $R^2$ may contain oxygen or sulfur atoms in the carbon chain. Ethers and thioethers containing such $R^1$ and $R^2$ groups, may be considered to be derivatives of polyhydroxy compounds such as glycol and glycerol. Examples of ethers wherein the $R^1$ and/or $R^2$ groups contain oxygen atoms in the carbon chain include 1,1-dimethoxyethane, diethyleneglycol, diethyleneglycol diethyl ether, diethyleneglycol monobutyl ether, diethyleneglycol monoethyl ether, diethyleneglycol monomethyl ether, ethyleneglycol ethyl ether, ethyleneglycol dimethyl ether, ethyleneglycol diethyl ether, 2-methoxy ethanol, 2-(2-methoxyethoxy) ethanol, etc.

The amount of ether or thioether mixed with the methane feedstock can be varied over a wide range and is an amount which is effective to assist in the desired conversion of the gaseous feedstock to liquid hydrocarbons. Generally, from about 0.1 to about 30% by volume of the ether or thioether is used based on the volume of the feedstock. More often the amount of ether or thioether will be in the range of 0.1 to 15%, and most often in the range of 1–10% by volume.

The conversion of methane and/or natural gas feedstocks to higher molecular weight liquid hydrocarbon products in accordance with this invention can be conducted at temperatures above about 800° C., and the temperatures may be as high as 1300° C. or 1500° C. Preferably, the pyrolysis reaction is conducted at temperatures between about 800° C. to about 1200° C. For methane gas, a preferred temperature is about 1000° C. to about 1200° C.

The pyrolysis reaction can be conducted at subatmospheric, atmospheric or at elevated pressures up to about 50 atmospheres. Generally, the reaction is conducted at a pressure of from about 1 to about 10 atmospheres, and more generally at about 1 to 3 atmospheres.

The period of time for heating the gaseous mixture of methane and/or natural gas and the ether or thioether (or residence time in the reactor) is generally a time which is sufficient to provide the desired conversion to higher molecular weight liquid hydrocarbon products. However, the reaction time or residence time should not be so long as to provide sufficient time for the products obtained to decompose. Accordingly, contact or residence times in the range of from about 0.1 to about 5000 milliseconds have been found to be useful with contact times in the range of from about 1 to about 1500 milliseconds generally being sufficient. Contact times of from about 20 to about 1000 milliseconds are most preferred.

The overall composition of the higher molecular weight hydrocarbon products produced in accordance with the process of the invention may vary somewhat depending upon the nature (source) of the methane and/or natural gas that are initially used as feedstock, and the condition under which they are processed. For example, the higher molecular weight hydrocarbon product will typically consist of hydrocarbons containing two or more carbon atoms. These hydrocarbon products generally consist of mixtures of both aliphatic and aromatic materials. Since the process of the present invention is well-suited to a continuous, cyclic process, the lighter weight gaseous hydrocarbon products such as ethane or propane, etc. can be separated from the more desirable higher molecular weight liquid hydrocarbon products and recycled in the process for further conversion to higher molecular weight liquid hydrocarbon products. Unsaturated hydrocarbons such as ethylene acetylene, propylene, etc., may be present in the gaseous hydrocarbon products obtained in this invention and these may be recycled through the process for conversion to higher molecular weight liquid products.

The preferred higher molecular weight hydrocarbon products made by the process of the present invention are aliphatic and/or aromatic products that are sufficiently liquid to be readily handleable and transportable in conventional pipeline systems. Included in this preferred group are hydrocarbons containing at least about 5 carbon atoms, more particularly, aromatic compounds containing at least 6 carbon atoms. The references in this application to "liquid hydrocarbons" are intended to include hydrocarbons that are substantially in the liquid form at a temperature of about 25° C. and a pressure of one atmosphere.

The apparatus used in the process of the present invention can be any conventional pyrolysis reactor system that is adapted to the specific gaseous reactants and high molecular weight products provided for in the process of the invention. Such pyrolysis reactors include fired tubular heaters, pebble-bed heaters and regenerative furnaces, but fired tubular heaters are the generally preferred type of reactor. These reactors can be made from a variety of materials which can withstand high temperatures. A more detailed description of such apparatus can be found in the Encyclopedia of Chemical Technology, Kirk and Othmer, Ed. Third Edition, Vol. 9, pp. 400-11 which is incorporated herein by reference. The design and construction of such apparatus is within the skill of the art and thus need not be described further herein.

In one preferred embodiment, the process of the invention is carried out in the absence of any solid catalyst, particularly solid aromatization catalysts. Such catalysts are not required in the present pyrolysis reaction.

In order to further illustrate the present invention, the following examples are provided. Unless otherwise indicated in the following examples and elsewhere in the specification and claims, all parts and percentages of products are by weight and those of the feed are by volume; all temperatures are in degrees centigrade.

In each of the following examples, the feedstock is introduced into a quartz tube reactor that is surrounded by an electric furnace to provide the desired temperature. The control samples contain no added ether or thioether. In operation, the gaseous feed composition is advanced through the quartz tube and the exiting product is cooled in containers with dry ice and acetone. The "liquids" identified in the following table are those materials which condense in the cooled containers. The weight percentage of the liquid products is calculated by weighing the liquids formed and dividing that weight by the amount of carbon and hydrogen in the feed and multiplying by 100. The selectivity is defined by dividing the weight of product formed by the weight of converted carbon and hydrogen in the feed and multiplying by 100. The conversion is defined by dividing the hydrocarbon that is converted by the hydrocarbon fed and multiplying by 100. The gases that are obtained from the process are analyzed using either a Carl 400GC or a Carl 311HGH chromatograph.

EXAMPLES C-1 AND 1

In these examples, methane is used as the feedstock. The pyrolysis temperature is 1100° C., the inner diameter of the quartz reactor is 10 mm., and the contact time is about 250 milliseconds. Example C-1 is a control in which no ether is added. In Example 1, 6% by volume of dimethyl ether is added to the methane feedstock. Other particulars of these examples, including the results are summarized in Table I. The data for Example 1 listed in Table I is an average of three runs. The results demonstrate the improvements obtained when dimethyl ether is added including increased methane conversion and formation of liquids, selectivity to liquids and reduced carbon formation.

TABLE I

| Example | C-1 | 1 |
|---|---|---|
| Feed: | | |
| CH₄ (% v) | 100 | 94 |
| Ether (% v) | — | 6 |
| Methane conv. (%) | 7.0 | 9.9 |
| Liquids formed (%) | 0.2 | 3.7 |
| Selectivity to liquids (%) | 2.6 | 15.4 |
| Selectivity to Carbon (%) | 3.8 | 0.5 |

EXAMPLES C-2 AND 2

In these examples, methane is used as the feedstock, the pyrolysis temperature is about 1125° C., the inner diameter of the quartz reactor is 5 mm., and the contact time is about 200 milliseconds. Example C-2 is a control in which no ether is added. In Example 2, the feedstock contains 5% by volume of dimethyl ether and 95% of methane. The results of these pyrolysis examples are summarized in Table II.

TABLE II

| Example | C-2 | 2 |
|---|---|---|
| Feed: | | |
| CH₄ (% v) | 100 | 95 |
| Ether (% v) | — | 5 |
| Methane conv. (%) | 3.6 | 6.5 |
| Liquids formed (%) | 1.4 | 4.1 |
| Selectivity to liquids (%) | 39.0 | 22.0 |

The results of these experiments demonstrate that the process of the present invention results in an increase in methane conversion and formation of liquids.

While the invention has been explained in relation to its preferred embodiments, it is to be understood that the various modifications thereof will become apparent to those skilled in the art upon reading this specification. Therefore, it is to be understood that the invention disclosed herein is intended to cover such modifications as fall within the scope of the appended claims.

We claim:

1. A thermal process for converting a feedstock comprising methane and/or natural gas to liquid hydrocarbons comprising heating a gaseous mixture comprising said feedstocks and a minor effective amount of at least one ether or thioether compound at a temperature of at least about 800° C. for a period of time effective to provide said liquid hydrocarbons.

2. The process of claim 1 wherein the feedstock comprises methane.

3. The process of claim 1 wherein the feedstock comprises natural gas.

4. The process of claim 1 wherein the ether and thioether are represented by the formula $$R^1XR^2$$

wherein $R^1$ and $R^2$ are each independently hydrocarbyl groups containing from 1 to about 10 carbon atoms, and X is oxygen or sulfur.

5. The process of claim 4 wherein $R^1$ and $R^2$ are each independently aliphatic, cycloaliphatic or aromatic hydrocarbyl groups.

6. The process of claim 4 wherein $R^1$ and $R^2$ are aliphatic or cycloaliphatic groups.

7. The process of claim 4 wherein $R^1$ and $R^2$ are independently alkyl, alkenyl or alkynyl groups.

8. The process of claim 4 wherein $R^1$ and $R^2$ are each independently alkyl groups containing up to about 6 carbon atoms.

9. The process of claim 4 wherein X is oxygen.

10. The process of claim 9 wherein $R^1$ and $R^2$ are each independently alkyl groups containing up to about 6 carbon atoms.

11. The process of claim 1 wherein from about 0.1 to about 30% by volume of the ether or thioether is added to the feedstock.

12. The process of claim 1 wherein the mixture is heated to a temperature of from about 800° C. to about 1500° C.

13. The process of claim 1 wherein the gaseous mixture is heated for a period of from about 0.1 to about 5000 milliseconds.

14. The process of claim 1 wherein the feedstock comprises methane and the gaseous mixture is heated to a temperature of from about 1000° C. to about 1200° C.

15. A thermal process for converting a feedstock comprising methane and/or natural gas to liquid hydrocarbons comprising heating a gaseous mixture comprising said feedstocks and from about 0.1 to about 30% by volume of an ether or thioether characterized by the formula $$R^1XR^2$$

wherein $R^1$ and $R^2$ are aliphatic, cycloaliphatic or aromatic hydrocarbyl groups containing up to about 10 carbon atoms, and X is oxygen or sulfur to a temperature of from about 800° C. to about 1500° C. for a period of time effective to provide said liquid hydrocarbons.

16. The process of claim 15 wherein the feedstock comprises natural gas.

17. The process of claim 15 wherein the feedstock comprises methane.

18. The process of claim 15 wherein the gaseous mixture comprises from about 0.1 to about 15% by volume of the ether or thioether based on the volume of feedstock.

19. The process of claim 15 wherein the gaseous mixture is heated for a period of from about 0.1 to about 5,000 milliseconds.

20. The process of claim 15 wherein the gaseous mixture is heated for a period of from about 20 to about 1000 milliseconds.

21. The process of claim 15 wherein the gaseous mixture is heated to a temperature within the range of from about 800° C. to about 1200° C.

22. The process of claim 15 wherein the feedstock comprises methane, and the gaseous mixture is heated to a temperature of from about 1000° C. to about 1200° C.

23. The process of claim 15 wherein X is oxygen.

24. The process of claim 15 wherein $R^1$ and $R^2$ are each independently aliphatic or cycloaliphatic hydrocarbyl groups.

25. The process of claim 15 wherein $R^1$ and $R^2$ are independently alkyl, alkenyl or alkynyl groups.

26. The process of claim 15 wherein $R^1$ and $R^2$ are independently alkyl groups containing up to about 6 carbon atoms.

27. A process for converting methane and/or natural gas feedstocks to higher molecular weight liquid hydrocarbon products which comprises heating a gaseous mixture comprising said feedstocks and from about 1 to about 10% by volume, based on the volume of said feed-stock, of at least one dialiphatic ether containing up to about 10 carbon atoms in the aliphatic groups to a temperature of from about 800° C. to about 1300° C. for a period of time of from about 20 to about 1000 milliseconds.

28. The process of claim 27 wherein the feedstock is natural gas.

29. The process of claim 27 wherein the feedstock is methane.

30. The process of claim 27 wherein the gaseous mixture is heated to a temperature between about 800° C. to about 1200° C.

31. The process of claim 27 wherein the feedstock comprises methane, and the gaseous mixture is heated to a temperature of from about 1000° C. to about 1200° C.

32. The process of claim 27 wherein the two aliphatic groups of the ether are each alkyl or alkenyl groups containing up to about 6 carbon atoms.

33. The process of claim 27 wherein the ether is dimethyl ether.

34. The process of claim 27 wherein the liquid hydrocarbon product is recovered from the gases, and the gases are recycled through the process.

* * * * *